United States Patent [19]

Lunn et al.

[11] 4,379,787

[45] Apr. 12, 1983

[54] OXIMINO-SUBSTITUTED CEPHALOSPORIN COMPOUNDS

[75] Inventors: William H. W. Lunn; William J. Wheeler, both of Indianapolis, Ind.

[73] Assignee: Eli Lilly and Company, Indianapolis, Ind.

[21] Appl. No.: 307,985

[22] Filed: Oct. 2, 1981

[51] Int. Cl.[3] .................. C07D 501/40; A61K 31/545

[52] U.S. Cl. ........................................ 424/246; 544/22; 544/25

[58] Field of Search ...................... 544/22, 25; 424/246

[56] References Cited

U.S. PATENT DOCUMENTS

| | | | |
|---|---|---|---|
| 4,200,575 | 4/1980 | Numata et al. | 424/246 |
| 4,258,041 | 3/1981 | O'Callaghan et al. | 424/246 |
| 4,267,176 | 5/1981 | Kamiya et al. | 424/246 |

OTHER PUBLICATIONS

Nomura et al., J. Med. Chem. 1974, vol. 17, No. 12, pp. 1312–1315.

Derwent Abstract 32890.

*Primary Examiner*—Robert Gerstl

*Attorney, Agent, or Firm*—William B. Scanlon; Arthur R. Whale

[57] ABSTRACT

Broad spectrum cephalosporin antibiotics represented by the formula

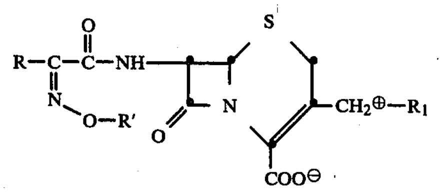

wherein R is an amino-substituted oxazole, oxadiazol, or isoxazole heterocyclic, R' is $C_1$-$C_4$ alkyl, a carboxysubstituted alkyl or cycloalkyl group, etc., and $^{\oplus}R_1$ is an oximino-substituted pyridinium, quinolinium or isoquinolinium group, e.g., $^{\oplus}R_1$ is a 3- or 4-formylpyridinium oxime group; pharmaceutical compositions comprising the antibiotic, and a method for treating antibacterial infections are provided.

23 Claims, No Drawings

OXIMINO-SUBSTITUTED CEPHALOSPORIN COMPOUNDS

BACKGROUND OF THE INVENTION

This invention relates to semi-synthetic cephalosporin antibiotic compounds. In particular, it relates to cephalosporin compounds represented by the following formula

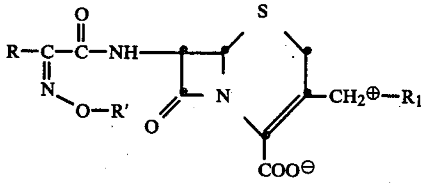

wherein R is a 5-membered hetrocyclic ring containing oxygen and nitrogen atoms, R' is hydrogen, $C_1$–$C_4$ alkyl, an N-substituted carbamoyl group or a carboxy-substituted alkyl or cycloalkyl group, and $^{\oplus}R_1$ is pyridinium, quinolinium, or isoquinolinium, each bearing an oximino substituent group.

The compounds of the invention are cephalosporin betaines characterized by the inner salt formed with the $C_4$ carboxylate anion and the cation of the quaternary heterocyclic group $^{\oplus}R_1$.

Cephalosporin antibiotics substituted in the 3'-position by a quaternary ammonium group have been known for some time. One of the first derivations of cephalosporin C which was discovered was cephalosporin $C_{A\ (pyridine)}$, Hale, Newton, and Abraham, *Biochem. J.*, 79, 403 (1961). Cephaloridine, the well-known clinical antibiotic is the 3'-pyridinium, 7-(α-thienylacetamido)-3-(pyridinium-1-ylmethyl)-3-cephem-4-carboxylate.

Recently, Heymes et al., U.S. Pat. No. 4,152,432, described semi-synthetic cephalosporin compounds having a 7-[2-(2-aminothiazol-4-yl)-2-alkoxyiminoacetamido] side chain group in the 7-position of the bicyclic cephem ring system, while the acetoxymethyl group is the 3-position substituent. Others have prepared 3'-pyridinium-substituted derivatives of this type of oximino-substituted cephalosporin. For example, Ochiai et al., U.S. Pat. No. 4,278,671 describe 7-[2-(2-aminothiazol-4-yl)-2-methoxyiminoacetamido]-3-(pyridinium-1-ylmethyl)-3-cephem-4-carboxylate, and O'Callaghan et al., U.S. Pat. No. 4,258,041, describe ceftazidime, 7-[2-(2-aminothiazol-4-yl)-2-(2-carboxyprop-2-yl)oxyiminoacetamido]-3-(pyridinium-1-ylmethyl)-3-cephem-4-carboxylate.

Continuing research with the cephalosporin antibiotics has as one of its goals the development of antibiotics to overcome the deficiencies in current antibiotic therapy. For example, there exists the need for cephalosporin antibiotics with greater potency against the gram-negative bacteria such as pseudomonas, and with inhibitory activity against microorganisms which are resistant to the presently known antibiotics.

The cephalosporin compounds of this invention are structurally novel compounds which possess high activity against the gram-negative bacteria with retention of high activity against the gram-positive microorganisms.

DETAILED DESCRIPTION

The cephalosporin compounds of the invention are represented by the following formula 1

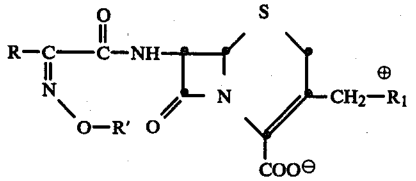 1 wherein R is an amino-substituted heterocyclic of the formula

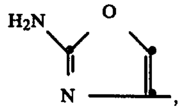,
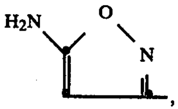, or
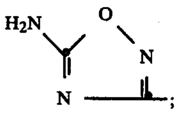;

R' is hydrogen, $C_1$–$C_4$ alkyl, a carboxy-substituted alkyl or a carboxy-substituted cycloalkyl group represented by the formula

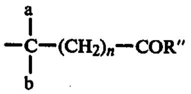

wherein a and b when taken separately are independently hydrogen or $C_1$–$C_3$ alkyl, and a and b when taken together with the carbon atom to which they are bonded form a $C_3$–$C_7$ carbocyclic ring; n is 0–3; and R'' is hydroxy, $C_1$–$C_4$ alkoxy, OR°, wherein R° is a carboxy-protecting group, or amino; or R' is a substituted carbamoyl group represented by the formula

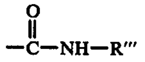

wherein R''' is $C_1$–$C_4$ alkyl, phenyl or $C_1$–$C_3$ alkyl substituted by phenyl; $R_1{}^{\oplus}$ is an oximino-substituted pyridinium, quinolinium, or isoquinolinium group represented by the formulas

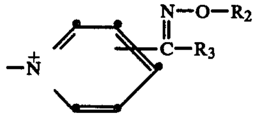

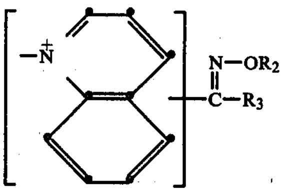

-continued

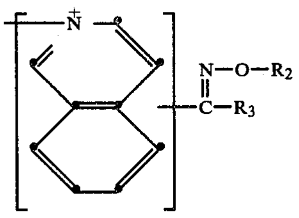

wherein $R_2$ and $R_3$ independently are hydrogen or $C_1$–$C_3$ alkyl; and the pharmaceutically acceptable non-toxic salts thereof.

In the definition of the above formula 1, the term "oximino" is used herein for convenience to refer to the

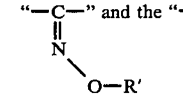
and the
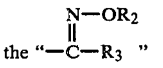

structural moieties of formula 1. The term "$C_1$–$C_4$ alkyl" refers to methyl, ethyl, n-propyl, isopropyl, n-butyl, sec-butyl, t-butyl and like straight and branched chain lower alkyl radicals; "$C_1$–$C_3$ alkyl substituted by phenyl" refers to benzyl, 2-phenethyl, 1-phenethyl, 3-phenylpropyl, and 2-phenylpropyl; and "$C_1$–$C_4$ alkoxy" refers to methoxy, ethoxy, n-propoxy, isopropoxy, t-butoxy, n-butoxy, sec-butoxy, and isobutoxy. "$C_1$–$C_3$ alkyl" refers to methyl, ethyl, n-propyl, and isopropyl.

Illustrative of the carboxy-substituted alkyl and cycloalkyl groups R′ wherein R″ is hydroxy are carboxymethyl, 2-carboxyethyl, 3-carboxypropyl, 2-carboxyprop-2-yl, 3-carboxypent-3-yl, 4-carboxyhept-4-yl, 2-(carboxymethyl)prop-2-yl, 2-(2-carboxyethyl)prop-2-yl, 1-carboxycycloprop-1-yl, 1-carboxycyclobut-1-yl, 1-carboxycyclohex-1-yl, 1-carboxycyclopent-1-yl, 1-(carboxymethyl)cyclopent-1-yl, 1-(2-carboxyethyl)cyclohex-1-yl, and 1-carboxycyclohept-1-yl. Examples of such groups when R″ is $C_1$–$C_4$ alkoxy are represented by the $C_1$–$C_4$ alkyl esters of the above-named carboxy-substituted alkyl and cycloalkyl radicals wherein R″ is hydroxy, for example, methoxycarbonylmethyl, ethoxycarbonylmethyl, n-propoxycarbonylmethyl, t-butoxycarbonylmethyl, ethoxycarbonylethyl, 1-methoxycarbonylcycloprop-1-yl, 2-ethoxycarbonylprop-2-yl, 1-ethoxycarbonylcyclopent-1-yl, and like esters. When in the formula 1 R″ is $NH_2$, the radicals represented are the primary amides of the above-named carboxy-substituted alkyl and cycloalkyl radicals, for example, aminocarbonylmethyl, 2-aminocarbonylethyl, 2-aminocarbonylprop-2-yl, 1-aminocarbonylcycloprop-1-yl, 1-aminocarbonylcyclobut-1-yl, and like amides.

The N-substituted carbamoyl radicals (R′ of formula 1) are illustrated by N-methylcarbamoyl, N-ethylcarbamoyl, N-ethylcarbamoyl, N-ethylcarbamoyl N-phenylcarbamoyl, N-benzylcarbamoyl, N-(2-phenylethyl)carbamoyl, and the like.

The carboxy group of the carboxy-substituted alkyl and cycloalkyl substituted compounds represented by the formula 1 (R″ is hydroxy) is desirably protected with a carboxy-protecting group (R°) during the preparation of compounds wherein R″ is hydroxy or a salt form thereof. Such carboxy-protecting groups are those commonly employed in the cephalosporin art to protect the carboxy group. Preferably, the protecting group is a readily removable ester-forming group. For example, the term R° can be t-butyl, 2-iodoethyl, 2,2,2-trichloroethyl, 2,2,2-tribromoethyl, allyl, 2-ethinylprop-2-yl, 2-vinylprop-2-yl, benzyl, p-methoxybenzyl, p-nitrobenzyl, diphenylmethyl, and like conventional carboxy-protecting groups which are removed under hydrolytic or hydrogenolytic conditions. Such groups function merely for the temporary protection of the carboxylic acid function to prevent its interaction during reactions carried out elsewhere in the molecule.

The heterocyclic group (R of formula 1) are named herein as follows: 2-aminooxazol-4-yl, 5-aminoisoxazol-3-yl, and 5-amino-1,2,4-oxadiazol-3-yl. Although depicted as amino-substituted heterocyclics, the tautomeric imino forms of the oxazole and oxadiazole heterocyclics can exist as illustrated below.

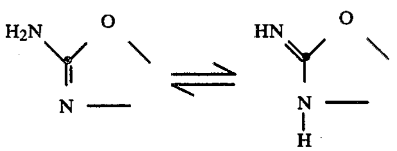

The compounds of the invention are characterized by an oximino-substituted pyridinium, quinolinium or isoquinolinium represented by the term ⊕R, in the formula 1. The compounds of the invention are also characterized as dioximino compounds by the oximino group in the 7-position side chain and the oximino-substituted group $⊕R_1$.

The compounds of the invention are prepared by the displacement of the acetoxy or halo group of a 3-acetoxymethyl- or 3-halomethyl-substituted cephalosporin respectively with an oximino-substituted pyridine, quinoline or isoquinoline ($R_1$).

Examples of the oximino-substituted pyridines, quinolines, and isoquinolines, which are used to prepare the compounds of the invention are the oximino-substituted pyridines such as 4-formylpyridine oxime, 4-formylpyridine methoxime, 3-formylpyridine oxime, 3-formylpyridine methoxime, 4-formylpyridine ethoxime, 3-formylpyridine n-propoxime, 2-formylpyridine oxime, 2-formylpyridine methoxime, 3-acetylpyridine oxime, 4-acetylpyridine oxime, 2-acetylpyridine oxime, 3-acetylpyridine methoxime, 3-acetylpyridine isopropoxime, 4-propionylpyridine oxime, 4-propionylpyridine methoxime, 4-butyrylpyridine oxime, 3-propionylpyridine ethoxime, 3-butyrylpyridine oxime, and like pyridine oximes; the quinoline and isoquinoline oximes such as 4-formylquinoline oxime, 4-formylisoquinoline oxime, 4-formylquinoline methoxime, 6-formylisoquinoline oxime, 4-formylquinoline methoxime, 6-formylisoquinoline methoxime, 6-formylquinoline oxime, 8-formylquinoline oxime, 8-formylisoquinoline methoxime, 6-formylisoquinoline ethoxime, 7-acetylquinoline oxime, 7-acetylquinoline n-butoxime, 5-acetylquinoline ethoxime, 6-propionylquinoline oxime, 6-propionylquinoline methoxime, 6-n-butyrylisoquinoline oxime, 5-acetylisoquinoline oxime, 5-acetylisoquinoline methoxime, 2-formylquinoline oxime, 1-formylisoquinoline methoxime, 3-formylquinoline oxime, 3-acetylquinoline oxime, 3-formylisoquinoline oxime, 3-formylisoquinoline isopropoxime, 3- acetylquinoline methoxime, and like quinoline and isoquinoline oximes.

The oximes $R_1$ are prepared by known methods, for example, by the condensation of hydroxylamine or a $C_1$–$C_3$ alkoxyamine with the formyl- or keto-substituted pyridine, quinoline or isoquinoline.

The preparation is illustrated below with the oximinopyridine

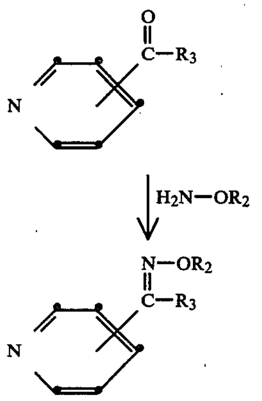

wherein $R_2$ and $R_3$ have the same meanings as defined for formula 1.

The compounds of the invention (formula 1) are prepared by alternative methods. According to one method, a 3-acetoxymethyl-substituted cephalosporin represented by the formula 2

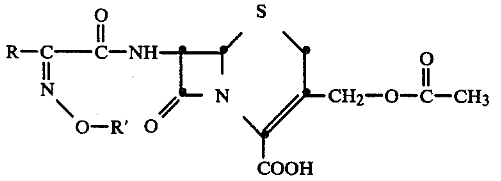

2 is allowed to react with the oximino-substituted pyridine, quinoline or isoquinoline, to provide a compound of the formula 1. The reaction is carried out by following known procedures for the preparation of 3'-pyridinium-substituted cephalosporins. For example, the compound of the formula 2 is reacted with the oximino-substituted heterocyclic base in an aqueous reaction medium at a temperature between about 25° C. and about 65° C. Aqueous reaction media comprise a water miscible organic solvent such as acetone, acetonitrile, tetrahydrofuran or other suitable solvent. In many instances a catalytic amount of an inorganic iodide salt such as sodium iodide or potassium iodide is added to the reaction mixture to enhance the rate and yield of the reaction.

According to another method for preparing the compounds represented by the formula 1, a 3-halomethyl-substituted cephalosporin is reacted with the oximino-substituted pyridine, quinoline, or isoquinoline to provide a compound of the invention. This method of preparation is illustrated by the following reaction scheme which employs an oximino-substituted pyridine example.

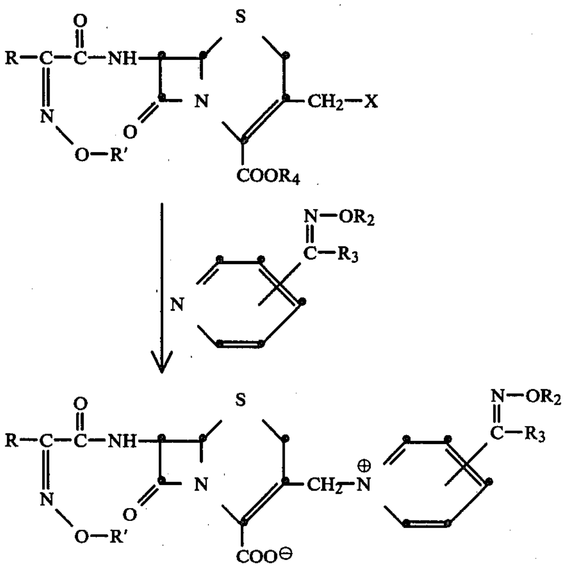

wherein X is chloro, bromo, or iodo and $R_4$ is a carboxy-protecting group. The carboxy-protecting group is preferably a silyl group which upon hydrolysis following displacement affords the compound of formula 1 as shown above. In the case where $R_4$ is a carbon ester such as one of the carboxy-protecting groups described hereinabove, the product of the displacement reaction is the betaine salt formed with the acid of the displaced halide, for example, the chloride, bromide or iodide salt. Upon removal of the carboxy-protecting group $R_4$, a compound of the invention is obtained.

The reaction is conveniently carried out at about room temperature or at somewhat elevated temperatures to about 50° C. Solvents which can be used for the reaction are inert aprotic organic solvents such as the chlorinated hydrocarbon solvents, methylene chloride, chloroform, trichloroethane, or other suitable solvent such as acetonitrile.

A solution of the oximino-substituted pyridine, quinoline, or isoquinoline in a suitable aprotic solvent, for example, one of the solvents mentioned above, is mixed with stirring with the solution of the 3-iodomethyl cephalosporin.

The oximino-substituted quinoline and isoquinoline compounds react similarly to provide the compound of the formula 1 wherein $^{\oplus}R_1$ is the oximino-substituted quinolinium or isoquinolinium group.

The preferred method for preparing the compounds of the invention comprises the use of the starting material in the above reaction scheme wherein X is iodo. These compounds are readily prepared by the method described by Bonjouklian, U.S. Pat. No. 4,266,049, issued May 5, 1981. According to the described method, a 3-acetoxymethyl-substituted cephalosporin or an ester thereof is reacted with a trialkylsilyliodide, for example, trimethylsilyliodide (TMSI), in an inert aprotic organic solvent under anhydrous conditions to provide the corresponding 3-iodomethylcephalosporin ester. In carrying out the preparation of a compound of the formula 1, a 3-acetoxymethyl cephalosporin substituted in the 7-position with the acyl group described for formula 1 is first silylated with a silylating agent to block the $C_4$ carboxy group, and, when R' is hydrogen or a carboxy-substituted alkyl or cycloalkyl group, the oxime hydroxy group and the carboxy group are protected as well. The silylating reagent can be any of a number of the commonly employed silylating agents, for example, mono-trimethylsilyltrifluoroacetamide (MSTFA), bis-trimethylsilylacetamide, or N-methyl-N-trimethylsilyl-trifluoroacetamide, and like reagents.

The silylated starting material is then reacted with a trialkylsilyliodide, for example, trimethylsilyliodide, to form the silylated 3-iodomethyl derivative represented in the above reaction scheme wherein $R_3$ is a trialkylsilyl group. Trimethylsilyliodide is the preferred trialkylsilyl iodide agent. The silylated 3-iodomethyl derivative is then reacted with the oximino-substituted pyridine, quinoline, or isoquinoline to provide the compound of the formula 1 in silylated form. Upon treatment of the reaction mixture with water, the compound of the formula 1 is obtained. The above-described preferred process is illustrated by the following reaction scheme.

2

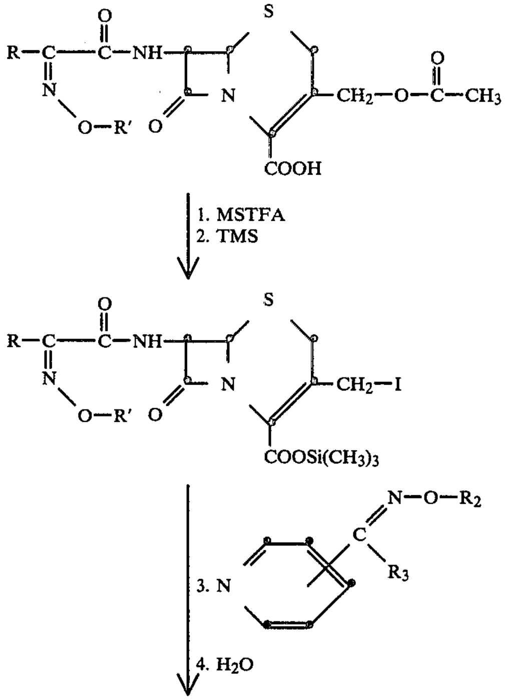

Formula 1

In an example of the preparation of a compound of the invention by the above preferred method, a suspension of 7-[2-(2-aminothiazol-4-yl)-2-methoxyiminoacetamido]-3-acetoxymethyl-3-cephem-4-carboxylate in chloroform is reacted with N-methyl-N-trimethylsilyltrifluoroacetamide at room temperature with stirring. After a complete solution is obtained, trimethylsilyliodide is added and the solution is stirred at room temperature. After between about 15 minutes and 1 hour of reaction time, the reaction mixture is evaporated to remove the solvent and the silylated 3-iodomethyl derivative is dissolved in dry acetonitrile and the solution treated with tetrahydrofuran. The treatment with tetrahydrofuran destroys any excess TMSI present in the reaction mixture. The solution is then mixed with a solution of the oximino-substituted pyridine, quinoline or isoquinoline compound in acetonitrile and the reaction mixture is stirred at about room temperature for between 1 and 6 hours. The reaction is best run under concentrated conditions such that when complete, the product precipitates from the reaction mixture upon treatment with the small amount of water sufficient to hydrolyze the silyl-blocking groups. The product being of ionic character precipitates from the organic reaction medium and is separated by filtration or centrifugation or other suitable means. The product at this point is generally crude and can be purified by $C_{18}$ silica reverse phase high performance liquid chromatography (HPLC) using a mixture of acetonitrile, acetic acid and water at a composition of about 10% acetonitrile, 2% acetic acid and 80% water.

The compounds of the invention also can be obtained by the acylation of a 7-amino-3-(oximino-substituted pyridinium, quinolinium or isoquinolinium)-3-cephem-4-carboxylate nucleus compound represented by the formula

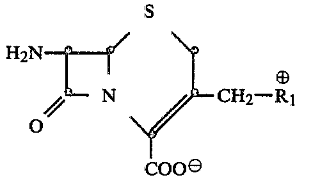

wherein $^{\oplus}R_1$ has the same meanings as defined for formula 1. The acylation is carried out with the oximino-substituted heterocyclicacetic acid represented by the formula 3

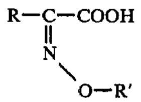

3 wherein R and R' are as defined for formula 1. An active derivative of the oximino acetic acid is best used in the acylation. For example, the acetic acid is converted to the hydroxybenzotriazole ester (HBT) by condensing the acid and hydroxybenzotriazole with a condensing agent such as a carbodiimide, eg. dicyclohexylcarbodiimide. The acetic acid HBT ester is then used to acylate the 7-amino nucleus compound. Other active derivatives of acetic acid can be used for purposes of the acylation. For example, the acid azide, acid halide, or the mixed anhydride types formed with the acetic acid and methyl chloroformate or isobutyl chloroformate, can be used.

During the acylation when R' of the acetic acid is hydrogen, the oxime group need not be protected; however, when R' is a carboxy-substituted alkyl or cycloalkyl group the free carboxy group thereof (formula 1, R'' is OH), is protected by a carboxy-protecting ester derivative (formula 1, R'' is OR°), for example, one of the R° groups mentioned hereinabove.

The 7-amino-3-(oximino-substituted pyridinium, quinolinium or isoquinolinium)-3-cephem-4-carboxylate nucleus compound used in the above acylation is prepared with 7-aminocephalosporanic acid (7ACA) as follows. 7ACA is converted to the N-formyl derivative and the latter is silylated and iodinated by following the procedures described hereinabove. The silylated N-formyl-3-iodomethyl-3-cephem-4-carboxylic acid is then reacted with the oximino-substituted pyridine, quinoline or isoquinoline and the product hydrolyzed to the 3'-substituted N-formyl nucleus compound. The product is deformylated with methanolic hydrochloric acid to provide the dihydrochloride salt form of the nucleus represented by the formula

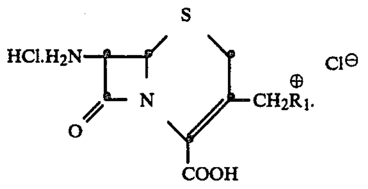

The latter salt form of the nucleus can be used for acylation or it can be converted to the $C_4$ carboxylate salt form for acylation.

The oximino-substituted heterocyclic acetic acid

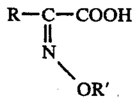

wherein R is 2-aminooxazole and R' is lower alkyl is prepared as illustrated by the following preparation of 2-(2-aminooxazol-4-yl)-2-methoxyiminoacetic acid wherein R' is methyl.

The 2-(2-aminooxazol-4-yl)-2-methoximinoacetic acid is first prepared as an ester by the zinc oxide catalyzed condensation of urea with an γ-bromo-α-methoximinoacetoacetic ester in a suitable organic solvent. Convenient esters are the methyl and ethyl esters. Suitable solvents are the ketones such as acetone, methylethylketone, diethylketone, or methylisobutylketone. The condensation is carried out by heating a suspension of zinc oxide in a solution of the urea and the bromoacetoacetic ester in the ketone solvent for about 60 hours to about 120 hours. The product is isolated by evaporating the reaction mixture and extracting the product from the concentrate with ethyl acetate. The ester product is purified by chromatography over alumina.

The 2-(2-aminooxazol-4-yl)-2-methoxyiminoacetic acid is prepared by the saponification of the above ester wherein the 2-amino group is protected. For example, ethyl 2-(2-aminooxazol-4-yl)-2-methoxyiminoacetate is reacted in dimethylacetamide with chloroacetyl chloride in the presence of an acid-binding agent such as a tertiary amine, e.g., triethylamine, to form the amino-protected derivative, 2-[2-(2-chloroacetamido)oxazol-4-yl]-2-methoxyiminoacetate. The latter is then deesterified with aqueous sodium hydroxide to sodium 2-(2-aminooxazol-4-yl)-2-methoxyiminoacetate. Upon acidification, the free acid is obtained. During the saponification, the amino-protecting chloroacetyl group is likewise removed.

The above-described preparation of the 2-aminooxazole oximino acid is illustrated by the following reaction scheme.

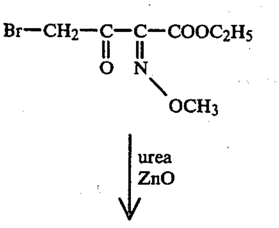

-continued

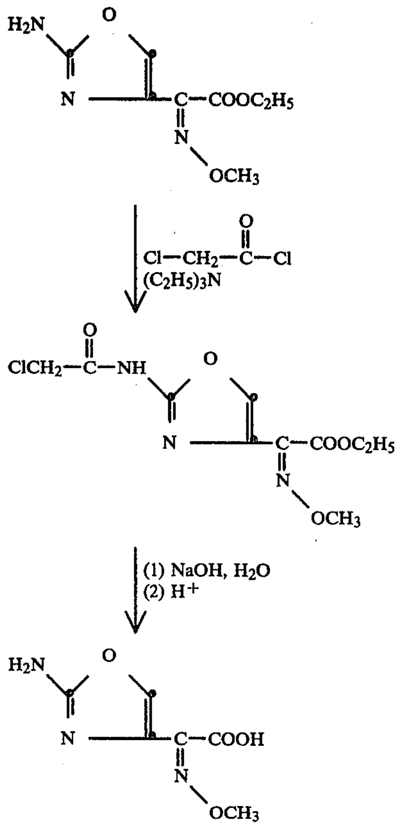

The above method for preparing the 2-(2-aminooxazol-4-yl)-2-methoximinoacetic acid is described by Wheeler in copending application Ser. No. 300,140, filed Sept. 8, 1981.

The 2-(5-amino-1,2,4-oxadiazol-3-yl)-2-methoximinoacetic acid (R is 5-amino-1,2,4-oxadiazol-3-yl, R' is methyl) is obtained according to the method described by Wheeler in copending application Ser. No. 300,159, filed Sept. 8, 1981. According to this method, ethyl 2-oximinocyano acetate is reacted with hydroxylamine to form 2-ethoxycarbonyl-2-methoximinoacetoxime amide as shown in the following reaction scheme.

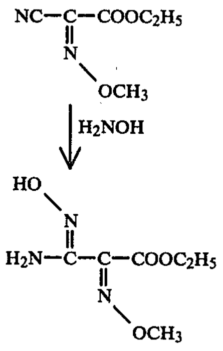

The latter intermediate is reacted with trichloroacetyl chloride to form the cyclized product, ethyl 2-(5-trichloromethyl-1,2,4-oxadiazol-3-yl)-2-methoximinoacetate, represented by the formula

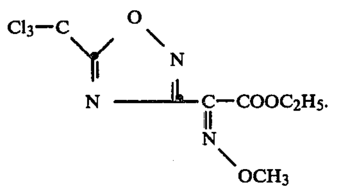

The trichloromethyl-substituted oxadiazole ester is reacted with ammonia to effect the replacement of the trichloromethyl group with an amino group and provide ethyl 2-(5-amino-1,2,4-oxadiazol-3-yl)-2-methoximinoacetate represented by the formula

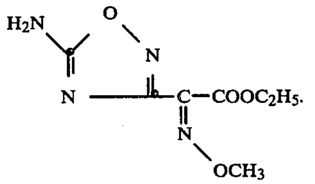

The trichloromethyl-substituted oxadiazole is a mixture of the syn and anti isomeric forms. During the aminolysis reaction, the anti isomer forms the amide, 2-(5-amino-1,2,4-oxadiazol-3-yl)-2-methoximinoacetamide, while the syn form of the intermediate does not. Owing to its lower solubility, the anti-amide is readily separated from the syn-ester.

The syn-ester is saponified in aqueous ethanolic sodium hydroxide to sodium syn-2-(5-amino-1,2,4-oxadiazol-3-yl)-2-methoximinoacetate and the free acid obtained by acidification of the sodium salt with hydrochloric acid.

The preparation of the 2-aminooxazole and 5-aminooxadiazole-substituted acetic acids (formula 3) wherein R′ is hydrogen is carried out as described above with the oxime protected by a hydroxy-protecting group such as the chloroacetyl group. During the saponification of the ethyl ester the chloroacetyl group is also removed.

The heterocyclic acetic acids represented by the formula 3 wherein R′ is a carboxy-substituted alkyl or cycloalkyl group, the 2-oximinocyano acetate represented by the formula

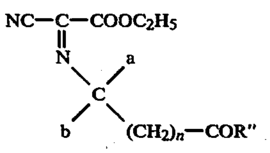

wherein R″ is $NH_2$, —OR°, or $C_1$–$C_4$ alkoxy, is used in the oxadiazole acetic acid preparative method described above, while the γ-bromo-α-oximinoacetoacetic ester represented by the formula

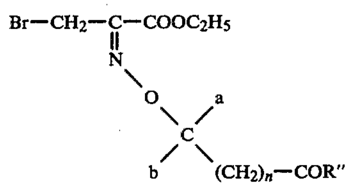

wherein R″ is $NH_2$, OR°, or $C_1$–$C_4$ alkoxy, is employed in the above-described oxazole acetic acid preparation method.

Following the preparation of the 2-aminooxazole and 5-aminooxadiazol acetic acids represented by the formula 3 wherein R′ is a carboxy-substituted alkyl or cycloalkyl group and R″ is —OR°, the carboxy-protecting ester group R° can be, for example, the p-methoxybenzyl or diphenylmethyl groups which are removed by known procedures on treatment in the cold (ca. 0° C.) with trifluoroacetic acid in the presence of anisole. The deesterified acids represented by the formula 3 wherein R′ is a carboxy-substituted alkyl or cycloalkyl group with R″ being OH are obtained. Alternatively, the R° ester group can be left intact until after the acetic acid (formula 3) is coupled with 7-aminocephalosporanic acid to obtain a compound of the formula 2, or is coupled with the 7-amino-3-(oximino-substituted pyridinium, quinolinium, or isoquinolinium methyl)-3-cephem-4-carboxylate to provide a compound of the invention (formula 1).

The heterocyclic-substituted acetic acid represented by the formula 3 wherein R′ is an N-substituted carbamoyl group are obtained by acylating the compound of the formula 3, wherein R′ is hydrogen, with the desired N-substituted carbamoyl chloride. During the acylation, the amino groups of the aminooxazole or aminoisoxazole acetic acids (formula 3) are protected; however, the amino group of the 5-amino-1,2,4-thiadiazole group lacks sufficient basicity to interfere in the acylation.

The compounds represented by the formula 2 hereinabove, which are used to prepare the compounds of the invention, are themselves prepared by the N-acylation of 7-aminocephalosporanic acid (7ACA) with an active carboxy-derivative of the heterocyclic acetic acid represented by the formula 3. The N-acylation is carried out by following known acylation procedures employed in the cephalosporin art for the N-acylation of 7ACA.

Examples of compounds of the invention are listed below.

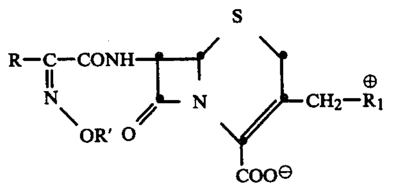

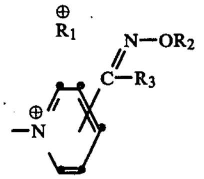

| R[1] | R' | $R_2$ | $R_3$ | Position |
|---|---|---|---|---|
| 2-AO | $CH_3$ | H | H | 3 |
| " | " | " | " | 4 |
| " | " | " | $CH_3$ | 3 |
| " | " | $CH_3$ | $CH_3$ | 4 |
| " | " | " | H | 3 |
| " | " | $C_2H_5$ | H | 4 |
| " | H | H | H | 3 |
| " | " | H | H | 4 |
| " | " | " | " | 2 |
| " | $-CH_2COOC_2H_5$ | H | H | 3 |
| " | " | H | $CH_3$ | 3 |
| " | " | H | $C_2H_5$ | 4 |
| " | $-C(CH_3)_2COOH$ | H | H | 3 |
| " | " | " | " | 4 |
| " | " | $CH_3$ | H | 3 |
| " | " | $CH_3$ | $CH_3$ | 4 |
| " | $-CH_2CH_2CONH_2$ | H | H | 3 |
| " | $-CONHCH_3$ | H | $CH_3$ | 4 |
| " | " | $CH_3$ | H | 3 |
| " | 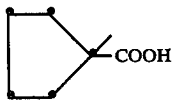 | H | H | 4 |
| " | 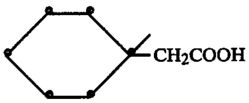 | H | H | 3 |
| " | $-CH(CH_3)_2$ | $CH_3$ | $CH_3$ | 2 |
| 5-AOD | H | H | H | 3 |
| " | " | " | " | 4 |
| " | $CH_3$ | " | " | 3 |
| " | " | " | " | 4 |
| " | " | $CH_3$ | " | 3 |
| " | " | " | $CH_3$ | 4 |
| " | " | " | " | 2 |
| " | $-CH_2COOC_2H_5$ | H | H | 3 |
| " | $-C(CH_3)_2COOH$ | H | H | 4 |
| " | " | H | H | 3 |
| " | " | $CH_3$ | H | 3 |
| " | " | H | $C_2H_5$ | 4 |
| 5-AIO | H | H | H | 3 |
| " | $CH_3$ | H | H | 3 |
| " | " | " | " | 4 |
| " | $C_2H_5$ | $CH_3$ | H | 4 |
| " | $-CH_2CH_2COOC_2H_5$ | H | $CH_3$ | 4 |

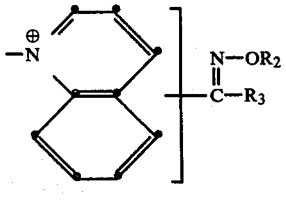

-continued

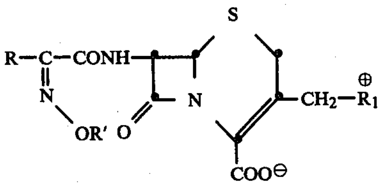

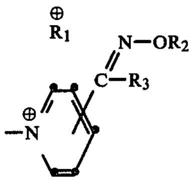

| R[1] | R' | $R_2$ | $R_3$ | Position |
|---|---|---|---|---|
| 2-AO | $CH_3$ | H | H | 3 |
| " | " | " | " | 4 |
| " | " | $CH_3$ | " | 3 |
| " | " | H | $CH_3$ | 4 |
| " | $-(CH_3)_2COOH$ | H | H | 3 |
| " | " | H | $CH_3$ | 4 |
| " | $-CH_2COOC_2H_5$ | $CH_3$ | $C_3H_7$ | 3 |
| " | $-C(CH_3)_2-CH_2CONH_2$ | H | H | 4 |
| " | $-CONHC_2H_5$ | H | $CH_3$ | 2 |
| 5-AOD | $CH_3$ | H | H | 3 |
| " | " | $CH_3$ | H | 3 |
| " | H | H | H | 2 |
| " | $-CH_2COOC_2H_5$ | H | $C_2H_5$ | 4 |
| " | $-C(CH_3)_2COONa$ | H | $CH_3$ | 3 |
| " | t-$C_4H_9$ | $CH_3$ | $CH_3$ | 4 |
| 5-AIO | H | H | H | 2 |
| " | " | " | " | 3 |
| " | $CH_3$ | H | $CH_3$ | 3 |
| " | $-CH_2COOC_2H_5$ | H | " | 4 |
| " | $-CONHC_6H_5$ | H | $C_3H_7$ | 4 |

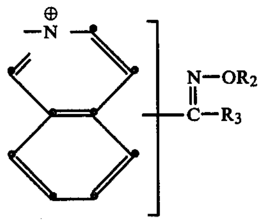

| | | | | |
|---|---|---|---|---|
| 2-AO | $CH_3$ | H | H | 3 |
| " | " | " | " | 4 |
| " | " | H | $CH_3$ | 3 |
| " | $-CH_2COOH$ | H | $CH_3$ | 4 |
| " | $-CH_2COOC_2H_5$ | H | H | 3 |
| " | $-C(CH_3)_2COOH$ | H | H | 3 |
| " | " | " | " | 4 |
| " | $-CH_2CONH_2$ | H | $CH_3$ | 3 |
| " | H | H | H | H |
| 5-AOD | $CH_3$ | H | H | 4 |
| " | " | H | $CH_3$ | 3 |
| " | " | $C_2H_5$ | " | 3 |
| " | $-CH_2COOC_2H_5$ | H | $CH_3$ | 4 |
| " | $-C(CH_3)_2COOH$ | H | H | 3 |
| " | $-(CH_2)_3COOCH_3$ | H | $CH_3$ | 4 |
| 5-AIO | H | H | H | 3 |
| " | $CH_3$ | H | H | 3 |
| " | " | H | $CH_3$ | 4 |
| " | $-CONHCH_3$ | $CH_3$ | $CH_3$ | 3 |

[1]2-AO is 2-aminooxazol-4-yl; 5-AOD is 5-amino-1,2,4-oxadiazol-3-yl; 5-AIO is 5-aminoisoxazol-3-yl.

The compounds of the invention (formula 1) form salts. Strong acids such as hydrochloric acid, hydrobromic acid, sulfuric acid, and phosphoric acid form salts of the type represented by the partial structural formula

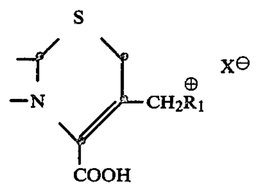

wherein $^{\oplus}R_1$ is as defined hereinabove and $X^{\ominus}$ is the anion formed with the strong acid. In general, acids having a pKa lower than that of the $C_4$ carboxylic acid group will form such salts.

Acid addition salts are also formed with the compounds of the formula 1 wherein R is the 2-aminooxazole or 5-aminoisoxazole. The basic amino group of these heterocyclics can form salts with acids such as hydrochloric acid, hydrobromic acid, sulfuric acid, phosphoric acid, methanesulfonic acid, and p-toluene sulfonic acid. Likewise, when R' of the formula 1 is a carboxy-substituted alkyl or cycloalkyl group (formula 1, R'' is hydroxy), the sodium and potassium salts of the carboxy group can be formed. The pharmaceutically acceptable non-toxic salts of such acid addition salts and salts of the carboxy group are useful forms of the antibiotics for administration of the antibiotics as well as for formulation purposes.

The compounds of the invention and the pharmaceutically acceptable non-toxic salts thereof are effective in controlling the growth of microorganisms pathogenic to man and animals. The compounds exhibit their antibacterial activity in vitro and in vivo against gram-positive and gram-negative bacteria. For example, the compounds are effective against proteus, serratia, klebsiella, haemophilus, pseudomonas, enterobacter, as well as the staphylococci and streptococci. Accordingly, the compounds of the invention are useful substances for the treatment and control of infectious diseases of man and animals.

A preferred group of compounds of the invention are represented by the formula 1 wherein $^{\oplus}R_1$ is a 3- or 4-oximino-substituted pyridinium group of the formula

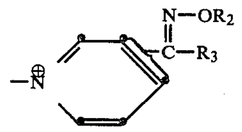

wherein $R_2$ is hydrogen and $R_3$ is hydrogen or methyl. A further preferred group of compounds are represented by the formula 1 wherein R is 2-aminooxazol-4-yl or 5-amino-1,2,4-oxadiazol-3-yl, and $^{\oplus}R_1$ is a 3- or 4-oximino-substituted pyridinium group of the above formula, and R' is $C_1$–$C_4$ alkyl or a carboxy-substituted alkyl group wherein R'' is hydroxy.

Examples of the preferred compounds are syn-7-[2-(5-amino-1,2,4-oxadiazol-3-yl)-2-methoxyiminoacetamido]-3-[(3-formylpyridinium oxime)-1-ylmethyl]-3-cephem-4-carboxylate, syn-7-[2-(2-aminooxazol-4-yl)-2-methoxyiminoacetamido]-3-[(4-formylpyridinium oxime)-1-ylmethyl]3-cephem-4-carboxylate, syn-7-[2-(2-aminooxazol-4-yl)-2-(2-carboxyprop-2-yl)oxyiminoacetamido]-3-[(3-formylpyridinium oxime)-1-ylmethyl]-3-cephem-4-carboxylate, syn-7-[2-(5-amino-1,2,4-oxadiazol-3-yl)-2(2-carboxyprop-2-yl)oxyiminoacetamido]-3-[(3-acetylpyridinium oxime)-1-ylmethyl]-3-cephem-4-carboxylate, syn-7-[2-(5-amino-1,2,4-oxadiazol-3-yl)-2-ethoxycarbonylmethoxyiminoacetamido]-3-[(4-acetylpyridinium oxime)-1-ylmethyl]-3-cephem-4-carboxylate, and syn-7-[2-(2-aminooxazol-4-yl)-2-(2-carboxyethoxyiminoacetamido]-3-[(3-acetylpyridinium oxime)1-ylmethyl]-3-cephem-4-carboxylate.

A further aspect of this invention provides a method for treating bacterial infections which comprises administering in an effective dose of between about 100 mg and about 2 g of a compound of the formula 1 or a pharmaceutically acceptable non-toxic salt thereof.

The antibiotic or a salt thereof can be administered intramuscularly (im), intravenously (iv) or subcutaneously (sc). Preferably, the compounds are administered via the im or iv route. The antibiotics may be administered in a single daily dose or in multiple daily doses, eg., three or four times a day. The treatment regimen may comprise administration of the antibiotic over a short duration of about one to three days or over a long duration of one to two weeks. The amount of the individual dose and the particular regimen will depend on such factors as the nature and severity of the infection, the general health and age of the patient as well as the tolerance of the individual to the antibiotic compound.

The antibiotics are administered by the iv route by the infusion method wherein the antibiotic is mixed with a physiologically acceptable fluid such as 5% dextrose, 0.9% saline or other suitable fluid. Such compositions are infused directly or, alternatively, by the piggyback method whereby a solution of the antibiotic is fed into a feeding tube also carrying a physiological fluid into the patient. For im administration, a solution of the antibiotic in a pharmaceutically acceptable diluent such as Water-for-Injection or 0.9% saline is made up and is administered by syringe.

In a further aspect of this invention, there are provided pharmaceutical formulations comprising a compound of the invention or a pharmaceutically acceptable non-toxic salt thereof and a pharmaceutical carrier. The pharmaceutical compositions can be prepared with the antibiotic or a salt thereof prior to use by incorporating the antibiotic at a concentration between about one percent and about twenty five percent in a diluent such as Water-for-Injection, or 0.9% saline for injection. The composition also may contain a solubilizing agent, stabilizing agent, buffering agent, clarifying agent or other pharmaceutical excipient.

Pharmaceutical compositions of the invention also include the antibiotic of the invention or a pharmaceutically acceptable salt thereof in dosage unit form. Such forms include the antibiotic or salt in solid form in a sterile vial or ampoule. The solid antibiotic may be amorphous or crystalline. Dosage unit forms of the invention contain between about 100 mg and about 5 g of the antibiotic. For example, one dosage unit form contains 250 mg. Another contains 500 mg of antibiotic per form. The dosage unit form may also contain an excipient such as a solubilizing agent, a stabilizing agent, a buffering agent, and like excipients. The dosage unit form is dissolved in a suitable diluent for administration via syringe or for iv infusion. Such diluents can be, for example, Water-for-Injection, 0.9% saline, or other suitable diluent. Preferred dosage unit formulations of this invention comprise a preferred compound of the invention.

The following Preparations and Examples further illustrate the invention. The abbreviations used in the Preparations and Examples have the following meanings: HPLC is high performance liquid chromatography; E refers to the anti form of the oxime; Z refers to the syn form of the oxime; DMSO/$d_6$ is deuterated dimethylsulfoxide; acetone/$d_6$ is deuterated acetone; n.m.r is nuclear magnetic resonance spectrum; the letters used to characterize the signals in the n.m.r. spectra refer to the following: s is singlet; d is doublet; q is quartet; m is multiplet; J is the coupling constant in Hertz; br s is broad singlet; and t is triplet.

PREPARATION 1

Preparation of 2-[(5-Amino-1,2,4-oxadiazol)3-yl]-2-methoxyimino Acetic Acid

Step A

Preparation of 2-Ethoxycarbonyl-2-methoximinoacetoxime Amide

Ethyl 2-methoxyiminocyanoacetate (8 g, 51.2 mmol) was dissolved in ethanol (2B, 20 ml) and the solution was added dropwise to a mixture of hydroxylamine hydrochloride salt (3.56 g, 51.2 mmol) and sodium carbonate (2.72 g, 25.6 mmol) in 3:2 v:v ethanol/water mixture (25 ml). After the addition was complete, the mixture was stirred and heated at the reflux temperature for approximately sixteen hours. The ethanol was then removed in vacuo and the remaining mixture was further diluted with water and then extracted with ethyl acetate. The ethyl acetate layer was washed with water (3X), dried over magnesium sulfate, filtered and concentrated to an oil in vacuo. The resultant oil later crystallized and was recrystallized from ethanol (2B) to yield 750 mg of the product, 2-ethoxycarbonyl-2-methoximinoacetoxime amide: n.m.r. ($d_6$-DMSO) δ0.82 (t, 3, $\underline{CH_3}CH_2$), 3.5 (s, 3, $O\underline{CH_3}$), 3.62 (q, 2, $CH_3\underline{CH_2}$—), 5.0 (br s, 2, —$\underline{NH_2}$), 10.15 (s, 1, =NOH).

Step B

Preparation of Ethyl 2-[(5-Trichloromethyl-1,2,4-oxadiazol)-3-yl]-2-methoxyimino Acetate 2-Ethoxycarbonyl-2-methoximinoacetoxime amide (7.65 g, 40 mmol) and pyridine (5 ml, 45 mmol) were dissolved in dioxane (25 ml) and the solution cooled to 10° C. While stirring this solution, trichloroacetyl chloride (5 ml, 45 mmol) was added dropwise. The mixture was then allowed to warm to room temperature and the stirring was continued for approximately sixteen hours. The mixture was filtered to remove the pyridine hydrochloride and the filtrate was evaporated to dryness.

The residue was triturated with ether and decanted. The ether layer was washed with a saturated aqueous solution of sodium bicarbonate (2X) and then with water (2X), dried over magnesium sulfate, filtered and concentrated. The solid mass remaining was triturated with hexane and decanted. The remaining solid, which was unreacted starting material, was recrystallized from methanol. The hexane solution from the above decantation was evaporated to yield the product compound, ethyl 2-[(5-trichloromethyl-1,2,4-oxadiazol)-3-yl]-2-methoxyimino acetate:(isomeric mixture)mass spectrum:M+ 315.

Step C

Preparation of Ethyl 2-[(5-Amino-1,2,4-oxadiazol)-3-yl]-2-Z-methoximinoacetate Ethyl 2-[(5-trichloromethyl-1,2,4-oxadiazol)-3-yl]-2-methoximinoacetate (7.62 g) was dissolved in ether (40 ml) and the solution added dropwise to anhydrous ammonia (250 ml) with stirring. Stirring was continued while the ammonia evaporated overnight. The residue was triturated thoroughly with ether. Filtration yielded 1.1 g of the undesired 2-[(5-amino-1,2,4-oxadiazol)-3-yl-2-Z-methoximinoacetamide. The filtrate from above was concentrated in vacuo then recrystallized from 2B ethanol to give 2.2 g of the crude title product.

The crude product was combined with ethyl 2-[(5-amino-1,2,4-oxadiazol)-3-yl]-2-Z-methoximinoacetate (0.83 g) made in a previous experiment analogous to the instant procedure. This mixture was dissolved partially in methylene chloride and filtered. The filtrate was chilled to −40° overnight then filtered again. The filtrate was evaporated to dryness and the residue was crystallized from 2B ethanol, yielding 0.209 g of crystals of the title product. The mother liquor of this crystallization was concentrated and the residue was also recrystallized from 2B ethanol, yielding 0.270 g of the title product. Combination of the yields of these two recrystallizations gave 0.479 g of the desired pure product, ethyl 2-[(5-amino-1,2,4-oxadiazol)-3-yl]-2-Z-methoximinoacetate: n.m.r. ($CDCl_3$) δ1.15 (t, 3, $\underline{CH_3}$—$CH_2$—O—), 3.95 (s, 3, $\underline{CH_3}O$—N) 4.25 (q, 2, $CH_3$—$\underline{CH_2}$—O), 8.05 (br s, 2, $NH_2$); i.r. (mull) in $cm^{-1}$, 3420 (NH), 1730 ($CO_2Et$), 1670; u.v. (methanol) λ=227 nm, ε=11,335.

Step D

Preparation of Sodium 2-[(5-Amino-1,2,4-oxadiazol)-3-yl]-2-Z-methoximinoacetate Ethyl 2-[(5-amino-1,2,4-oxadiazol)-3-yl]-2-Z-methoximinoacetate (4.29 g, 20 mmol) was dissolved in 2B ethanol (50 ml), followed by addition of 5 N sodium hydroxide solution (4 ml). This reaction mixture was stirred for 0.75 hour at room temperature, then filtered. The solid collected was washed with 2B ethanol and ether to yield 3.43 g (82% yield) of cream-colored crystals of sodium 2-[(5-amino-1,2,4-oxadiazol)-3-yl]-2-Z-methoximinoacetate: i.r. (KBr) 1680, 1665, 1615; u.v. (methanol) $\lambda_{max}$=233, ε=10,391;

Analysis: Calculated for $C_5H_5N_4O_4Na$: C, 28.86; H, 2.42; N, 26.92; Found: C, 27.37; H, 2.91; N, 23.91.

Step E

Preparation of 2-[(5-Amino-1,2,4-oxadiazol)-3-yl]-2-Z-methoximnoacetic Acid Sodium 2-[(5-amino-1,2,4-oxadiazol)-3-yl]-2-Z-methoximinoacetate (1.0 g.) was suspended in ethyl acetate and 1 N hydrochloric acid was added dropwise (6 ml). The layers were separated and the aqueous layer was rewashed with ethyl acetate. The ethyl acetate layers were combined, dried over magnesium sulfate, filtered and the filtrate was evaporated to yield 0.75 g of 2-[(5-amino-1,2,4-oxadiazol)-3-yl]-2-Z-methoximinoacetic acid: n.m.r. ($CDCl_3$): δ4.0 (s, 3, N—$O\underline{CH_3}$), 7.05

(s, 2, N$\underline{H}_2$), 8.5 (s, 1, $CO_2H$), (DMSO/$d_6$) δ3.75 (s, 3, N—O$\underline{M}$e), 8.12 (s, 2, $NH_2$).

PREPARATION 2

Preparation of Benzhydryl 7β-[2-[(5-amino-1,2,4-oxadiazol)-3-yl]-2-Z-methoximinoacetamido]-3-acetoxymethyl-3-cephem-4-carboxylate 2-[(5-Amino-1,2,4-oxadiazol)-3-yl]-2-Z-methoximinoacetic acid (0.75 g, 4 mmol) was dissolved in a 1:1 v:v tetrahydrofuran/acetonitrile solvent (20 ml). This solution was stirred as dicyclohexylcarbodiimide (0.5 g, 2.4 mmol), dissolved in the same THF/acetonitrile solvent as above (10 ml), and was added dropwise. The resultant mixture was stirred for 0.5 hour, during which time the dicyclohexylurea precipitated. Benzhydryl7β-amino-3-acetoxymethyl-3-cephem-4-carboxylate (0.876 g, 2.0 mmol) was added to the solution and stirring was continued for 56 hours. The dicyclohexylurea was collected by filtration and the filtrate was evaporated, triturated with ether and decanted (2X). The ether-insoluble material was dissolved in ethyl acetate, washed with 1 N hydrochloric acid (2X), aqueous sodium bicarbonate solution (2X), and saturated sodium chloride solution (2X). This solution was then dried over magnesium sulfate, filtered and concentrated in vacuo. The resultant material was again triturated with ether and filtered, yielding 0.640 g of crude material. This material was purified by dry silica gel column chromatography, collecting 25 ml fractions. A 1:1 v:v ethyl acetate/cyclohexane solution was used as the eluant for the first 25 fractions, followed by elution with a 3:1 v:v ethyl acetate/cyclohexane solvent. Fractions 33 through 42 were combined, evaporated to dryness, dissolved in chloroform and precipitated from the chloroform by the addition of hexane. The precipitate was collected by filtration, washed with ether then dried in vacuo, yielding 0.420 g of benzhydryl 7β-[2-[(5-amino-1,2,4-oxadiazol)-3-yl]-2-Z-methoximinoacetamido]-3-acetoxymethyl-3-cephem-4-carboxylate: n.m.r. ($CDCl_3$) δ1.90 (s, 3, 3'-OAc), 3.27, 3.55 (ABq, J=6, 2, $C_2$-methylene proton), 4.68, 4.95 (ABq, J=5, 2, $C_3$-methine proton), 4.96 (d, J=1.5, 1, C-6 proton), 5.95 (dd, (J=1.5, 3), 1, C-7 proton), 6.25, (br s, 2, N$\underline{H}_2$), 6.85 (s, 1, C$\underline{H}Ph_2$), 7.20 (s, 10, aromatic protons), 8.72 (d, J=3, 1, 7-amido proton).

PREPARATION 3

Preparation of 7β-[2-(5-Amino-1,2,4-oxadiazol)-3-yl-2-Z-methoximinoacetamido]-3-acetoxymethyl-3-cephem-4-carboxylic Acid Benzhydryl 7β-[2-(5-amino-1,2,4-oxadiazol)-3-yl-2-Z-methoximinoacetamido]-3-acetoxymethyl-3-cephem-4-carboxylate (0.435 g) was dissolved in a formic acid solution (12 ml, 97–100%) of triethylsilane (0.3 ml) and stirred for 3 hours. The solution was evaporated to dryness, the residue dissolved in ethyl acetate and extracted with 10% aqueous sodium bicarbonate. The sodium bicarbonate solution was washed with ethyl acetate, then layered with ethyl acetate, and the resultant solution was acidified to pH 2 with 1 N hydrochloric acid. The ethyl acetate layer was separated and was washed with saturated sodium chloride solution, dried over magnesium sulfate and filtered. The filtrate was concentrated in vacuo and the residue triturated with ether and filtered to yield 0.215 g of the product compound 7β-[2-(5-amino-1,2,4-oxadiazol)-3-yl-2-Z-methoximinoacetamido]-3-acetoxymethyl-3-cephem-4-carboxylic acid: n.m.r. (acetone/$d_6$) δ1.7 (s, 3, OAc), 3.15, 3.42 (ABq, (J=6), 2, C-2 methylene protons), 3.67 (s, 3, N—OC$\underline{H}_3$), 4.57, 4.8 (ABq, J=5), 2, C-3 methylene proton), 4.87 (d, (J=2), 1, C-6 proton), 5.65 (dd, (J=2, 2.5), 1, C-7 protons), 7.05 (br s, 2, —N$\underline{H}_2$), 8.25 (d, J=2.5, 1, 7-amido proton).

PREPARATION 4

2-(2-Aminooxazol-4-yl)-2-Z-methoxyiminoacetic Acid

Ethyl γ-bromo-α-methoximinoacetoacetate (100 g, 0.397 mmol) and urea (91 g, 1.98 mmol) were dissolved in methylethylketone (3 l) and zinc oxide (16 g, 0.198 mmol) were added. The suspension was stirred under reflux for 48 hours and was then allowed to cool. The solution was filtered and concentrated in vacuo. The dark residue was dissolved in ethyl acetate and the solution filtered. The filtrate was evaporated in vacuo and the residue was chromatographed over Activity III neutral alumina. The column eluted sequentially with neat cyclohexane (1000 ml), 1:9 v:v ethyl acetate:cyclohexane (1000 ml), 2:8 v:v ethyl acetate:cyclohexane (2000 ml), 3:7 v:v ethyl acetate:cyclohexane (500 ml), and finally with 1:1 v:v ethyl acetate:cyclohexane until no more product was eluted. Fifty-five fractions were taken, although fractions 51 through 55 were 500 ml or greater. The crude product was contained in fractions 51, 52, and 53. The three fractions were evaporated to give a semi-crystalline mass, each of which were triturated with ether and filtered to yield 3 pure crops of crystals of product. These crops of crystals were combined with a second crop of crystals obtained from fraction 52 to yield 8.9 g of ethyl 2-[2-aminoxazol-4-yl]-2-Z-methoximinoacetate.

A mixture of ethyl 2-[2-aminooxazol-4-yl]-2-Z-methoximinoacetate (2.13 g, 10 mmol), triethylamine (1.53 ml, 11 mmol) and dimethylacetamide (25 ml) were chilled to 0° C. by means of an ice bath. A chilled solution of chloroacetyl chloride (0.939 ml, 11 mmol) in 10 ml of dimethylacetamide was added dropwise to the stirred solution. The reaction mixture was stirred for 0.5 hour at 0° C., and for 19 hours at room temperature. The reaction mixture was poured onto ice and the resultant mixture was extracted with ethyl acetate. The ethyl acetate was washed with water, dried over anhydrous magnesium sulfate, filtered and concentrated in vacuo. After evacuating under high vacuum for 24 hours, the residue was triturated with ether and filtered. The mother liquor was evaporated and the residue was recrystallized from carbon tetrachloride to give 0.456 g. of ethyl 2-[2-(2-chloroacetamido)oxazol-4-yl]-2-Z-methoximinoacetate; melting point 91°–92° C.; n.m.r. ($CDCl_3$) δ1.32 (t, 3, —C$\underline{H}_3$, J=7.5 Hz), 4.0 (s, 3, OC$\underline{H}_3$), 4.1 (s, 2, Cl—C$\underline{H}_2$—), 4.37 (q, 2, —O—C$\underline{H}_2$—, j=7.5 Hz), 7.25 (s, 1, aromatic proton).

Sodium hydroxide (5 N, 2 equivalents plus a 10% excess, 4.6 ml., 22.86 mmol) was added dropwise to a stirred suspension of ethyl 2-[2-(chloroacetamido)oxazol-4-yl]-2-Z-methoximinoacetate (3.0 g, 10.38 mmol) in water (90 ml). Dissolution of the ester was complete within about 15 to 20 minutes, and stirring was continued for an additional hour. The mixture was chilled and acidified by the dropwise addition of 1 N hydrochloric acid (6 ml). The aqueous layer was saturated with sodium chloride and the mixture was extracted with large quantities of ethyl acetate. The ethyl acetate extracts were dried over anhydrous sodium sulfate, filtered, combined and concentrated in vacuo, yielding 0.453 g of 2-(2-aminooxazol-4-yl)-2-Z-methoximinoacetic acid; melting point 170°–174° C. (decompose); n.m.r. (DMSO/$d_6$) δ3.84 (s, 3, NOC$\underline{H}_3$), 6.77 (br, s, 2, amino), δ7.48 (s, 1, aromatic proton).

PREPARATION 5

Benzhydryl 7β-[2-(2-Aminooxazol-4-yl)-2-Z-methoximinoacetamido]-3-acetoxymethyl-3-cephem-4-carboxylate 2-(2-Aminooxazol-4-yl)-2-Z-methoximinoacetic acid (0.261 g, 1 mmol) was dissolved in a mixture of dimethylacetamide (3 ml) and methylene chloride (3 ml). Triethylamine (0.139 ml, 1 mmol) was added to this solution and the resultant mixture was added dropwise to a stirred, chilled solution of iso-butyl-chlorocarbonate in 25 ml of methylene chloride. The reaction mixture was stirred for 1 hour, at the end of which time a methylene chloride (5 ml) solution of benzhydryl 7β-amino-3-acetoxymethyl-3-cephem-4-carboxylate was added dropwise. Initially, the reaction mixture was stirred at 0° to 10° C. and was allowed to gradually warm to ambient temperature and stirred overnight.

The reaction mixture was evaporated in vacuo and the residue was taken up in ethyl acetate. The ethyl acetate solution was washed sequentially with 1 N hydrochloric acid, 10% aqueous sodium bicarbonate, and a saturated aqueous sodium chloride solution. Removal of the ethyl acetate solvent in vacuo, after drying the solution over sodium sulfate and filtering, resulted in a yellow foam. This crude product mixture was chromatographed over Activity III Silica Gel (100–200 mesh, Woehlm). Elution was begun with 7:3 v:v ethyl acetate:cyclohexane (fractions 1 through 19), then neat ethyl acetate (fractions 20 through 34), and finally 9:1 v:v ethyl acetate:methanol (fractions 34 through 37). The desired product, benzhydryl 7β-[2-(2-aminooxazol-4-yl)-2-Z-methoximinoacetamido]-3-acetoxymethyl-3-cephem-4-carboxylate, was contained in fractions 14 through 30, and these fractions were combined to yield 0.100 g of the desired product: n.m.r. ($CDCl_3$) δ1.98 (s, 3, methyl of 3-acetoxymethyl), 3.3 and 3.56 (ABq, 2, C-2), 4.75 and 5.01 (ABq, 2, C-3'), 5.02 (d, 1, C-6), 5.25 (br, s, 2, amino), 5.95 (q, 1, C-7), 7.9) (s, 1, benzhydryl methine proton), 7.3 (m, 11, phenyl rings and oxazole ring), 8.42 (d, 1, amido proton).

PREPARATION 6

7β-[2-(2-Aminooxazol-4-yl)-2-Z-methoximinoacetamido]-3-acetoxymethyl-3-cephem-4-carboxylic Acid Benzhydryl 7β-[2-(2-aminooxazol-4-yl)-2-Z-methoximinoacetamido]-3-acetoxymethyl-3-cephem-4-carboxylate (approximately 100 mg, 0.16 mmol) was dissolved in a mixture of formic acid (97–100%), 4 ml) and triethylsilane (0.04 ml, 0.25 mmol). The reaction mixture was stirred at room temperature for 3 hours, was distilled with ethyl acetate, and evaporated to a gum. The gum was treated twice with an ethyl acetate/acetonitrile mixture to give a light-brown powder. The powder was further dried by evaporation in vacuo for 1 hour. The brown powder was then dried with ether for 0.5 hour, sonnicated, filtered and air-dried to yield 64 mg (91%) of 7β-[2-(2-aminooxazol-4-yl)-2-Z-methoximinoacetamido]-3-acetoxymethyl-3-cephem-4-carboxylic acid. n.m.r. (DMSO/$d_6$) δ2.0 (s, 3, acetoxymethyl methyl), 3.4 (m, 2, C-2), 3.85 (s, 3, =NOC$\underline{H}_3$), 4.85 (q, 2, J=16, C-3'), 5.15 (d, 1, J=6, C-6), 5.8 (q, 1, J=4, C-7), 6.85 (s, 2, amino), 7.5 (s, 1, oxazole ring), 9.6 (d, 1, J=9, amido).

Preparation 7

7β-[2-(2-Aminooxazol-4-yl)-2-Z-methoxyiminoacetamido]-3-acetoxymethyl-3-cephem-4-carboxylic Acid A mixture of 1-hydroxybenzotriazole monohydrate (1.02 g, 6.68 mmol) and triethylamine (1.138 ml, 8.16 mmol) in dimethylacetamide (8 ml) was chilled in an ice-acetone bath and a solution of methanesulfonyl chloride (0.57 ml, 7.3 mmol) in 2 ml of dimethylacetamide was added dropwise. The solution was stirred at 0° to 10° C. for 1.5 hours. A solution of 2-(2-aminooxazol-4-yl)-2-Z-methoximinoacetic acid (1.235 g, 6.68 mmol) in dimethylacetamide (2.5 ml) containing triethylamine (1.01 ml) was then added dropwise to the cold mixture, and the solution was stirred at 0° to 10° C. for an additional 1.5 hours. Water (21 ml) was then added dropwise and within 10 minutes after the water had been added, the product precipitated, was collected by filtration, washed with cold water, and ddried in vacuo to yield 1.277 g (63%) of the product, 1-(N-oxide)benzotriazol-3-yl 2-[2-aminooxazol-4-yl]-2-Z-methoximinoacetamide.

7β-Amino-3-acetoxymethyl-3-cephem-4-carboxylic acid (0.43 g, 1.58 mmol) was suspended in 25 ml of a 1:1, v:v, water:acetone solvent cooled in an ice bath and triethylamine (0.2 ml, 1.48 mmol) was added dropwise to the stirred solution. After the solution formed, 1-(N-oxide)benzotriazol-3-yl 2-[2-aminooxazol-4-yl]-2-Z-methoximinoacetamide (0.5 g, 1.66 mmol) was added portionwise. The pH of the solution was maintained at approximately 7.5 by the periodic additions of 45% aqueous potassium phosphate solution. After the addition of the benzotriazole amide was complete, the mixture was slowly allowed to warm to room temperature. After approximately 2 hours, dissolution had occurred and the solution was stirred overnight. The acetone was removed, and the aqueous concentrate was diluted with water, layered with ethyl acetate, and the pH of the solution adjusted to pH 2.5 by the addition of 1 N hydrochloric acid. The ethyl acetate layer was then separated, dried, filtered and evaporated in vacuo. The partially crystalline residue triturated with ether and filtered to yield 0.3 g of 7β-[2-(2-aminooxazol-4-yl)-2-Z-methoxyiminoacetamido]-3-acetoxymethyl-3-cephem-4-carboxylic acid: n.m.r. (DMSO/$d_6$) δ2.0 (s, 3, OAc), 3.32 and 3.61 (ABq, 2, J=18 Hz, C-2 protons), 4.85 (s, 3, OC$\underline{H}_3$), 4.7 and 5.0 (ABq, 2, J=12 Hz, C-3' protons), 5.08 (d, 1, J=4.5 Hz, C-6 proton), 5.72 (q, 1, J=4.5 and 9 Hz, C-7 proton), 6.6 (br, s, 2, amino), 7.38 (s, 1, oxazole aromatic proton), 9.5 (d, 1, J=9 Hz, 7-amido N-proton); u.v. (methanol) λmax=217 ($\epsilon_m$=19,254), λmax=265 ($\epsilon_m$=10,200);

Analysis Calculated: C, 43.74; H, 3.90; N, 15.94. Found: C, 44.01; H, 3.97; N, 15.75.

EXAMPLE 1

7-[2-(5-Amino-1,2,4-oxadiazol-3-yl)-2-Z-methoxyiminoacetamido]-3-[(4-formylpyridinium oxime)-31-ylmethyl]-3-cephem-4-carboxylate A suspension of 7-[2-(5-amino-1,2,4-oxadiazol-3-yl)-2-methoxyiminoacetamido]-3-acetoxymethyl-3-cephem- 4-carboxylic acid in chloroform is treated with stirring at room temperature N-methyl-N-trimethylsilyltrifluoroacetamide until a solution of the silylated derivative is obtained. To the solution is added at room temperature a 3–4 molar excess of the trimethylsilyliodide (TMSI) and the reaction mixture is stirred for about one hour. The reaction mixture containing the silylated 3-iodomethyl derivative is evaporated to remove volatiles and the concentrate is dissolved in acetonitrile. The solution is treated with stirring at room temperature with tetrahydrofuran in an amount sufficient to destroy the excess TMSI.

To the solution is added a solution of 4-formylpyridine oxime in acetonitrile and the mixture is stirred for about 3–4 hours at room temperature. The reaction mixture is then treated with sufficient water to hydrolyze the silyl groups, excess water being avoided. The product precipitates from the reaction mixture when the reaction is carried out at high concentration. Alternatively, if carried out in a dilute reaction mixture, the product is precipitated by treatment of the mixture with diethyl ether. The product can be purified by HPLC using $C_{18}$ silica gel reversed phase chromatography using acetonitrile-acetic acid-water, comprising about 1 to 20% acetonitrile and about 2% acetic acid.

EXAMPLE 2

7-[2-(5-Amino-1,2,4-oxadiazol-3-yl)-2-Z-methoxyiminoacetamido]-3-[(3-acetylpyridinium oxime)-1-ylmethyl]-3-cephem-4-carboxylate is prepared with the silylated 3-iodomethyl derivative obtained with 7-[2-(5-amino-1,2,4-oxadiazol-3-yl)-2-Z-methoxyiminoacetamido]-3-acetoxymethyl-3-cephem-4-carboxylic acid by the procedures of Example 1 and 3-acetylpyridine oxime.

EXAMPLE 3

7-[2-(5-Amino-1,2,4-oxadiazol-3-yl)-2-Z-methoxyiminoacetamido]-3-[(4-formylisoquinoliniumoxime)-2-ylmethyl]-3-cephem-4-carboxylae is prepared with silylated 7-[2-(5-amino-1,2,4-oxadiazol-3-yl)-2-Z-methoxyiminoacetamido]-3-iodomethyl-3-cephem-4-carboxylic acid and 4-formylisoquinoline oxime.

EXAMPLE 4

7-[2-(5-Amino-1,2,4-oxadiazol-3-yl)-2-Z-(2-carboxyprop-2-yl)oxyiminoacetamido]-3-[(3-formylpyridinium methoxime)-1-ylmethyl]-3-cephem-4-carboxylate is prepared by silylating 7-[2-(5-amino-1,2,4-oxadiazol-3-yl)-2-Z-(2-carboxyprop-2-yl)oxyiminoacetamido]-3-acetoxymethyl-3-cephem-4-carboxylic acid with N-methyl-N-trimethylsilyltrifluoroacetamide and reacting the silyl derivative with TMSI to obtain the silylated 3-iodomethyl derivative. The latter is reacted, according to Example 1, with 3-formylpyridine methoxime to obtain the title compound.

EXAMPLE 5

7-[2-(2-Aminothiazol-4-yl)-2-Z-methoxyiminoacetamido]-3-[(3-formylpyridinium oxime)-1-ylmethyl]-3-cephem-4-carboxylic is prepared by converting 7-[2-(2-aminooxazol-4-yl)-2-Z-methoxyiminoacetamido]-3-acetoxymethyl-3-cephem-4-carboxylic acid to the silylated 3-iodomethyl derivative by following the silylation and iodination procedures employing N-methyl-N-trimethylsilyltrifluoroacetamide and TMSI respectively as described by Example 1, and then reacting the silylated 3-iodomethyl derivative with 3-formylpyridine oxime to form the silylated title compound which on hydrolysis of the silyl groups affords the title compound.

EXAMPLE 6

7-[2-(2-Aminooxazol-4-yl)-2-Z-methoxyiminoacetamido]-3-[(5-acetylquinolinium oxime)-1-ylmethyl]-3-cephem-4-carboxylate is prepared with the corresponding 3-iodomethyl silylated derivative and 5-acetylquinoline oxime.

EXAMPLE 7

7-[2-(5-Aminoisoxazol-3-yl)-2-Z-methoxyiminoacetamido]-3-[(4-formylpyridinium ethoxime)-1-ylmethyl]-3-cephem-4-carboxylate is prepared with the corresponding silylated 3-iodomethyl derivative and 4-formylpyridine ethoxime.

EXAMPLE 8

7-[2-(2-Aminooxazol-4-yl)-2-Z-(2-carboxyprop-2-yl)oxyiminoacetamido]-3-[(4-acetylpyridinium oxime)-1-ylmethyl]-3-cephem-4-carboxylate is prepared by converting trimethylsilylated 7-[2-(2-aminooxazol-4-yl)-2-Z-(2-carboxyprop-2-yl)oxyiminoacetamido]-3-acetoxymethyl-3-cephem-4-carboxylic acid to the 3-iodomethyl derivative with TMSI, and reacting the 3-iodomethyl compound with 4-acetylpyridine oxime. The latter is hydrolyzed to the title compound.

We claim:

1. A compound of the formula

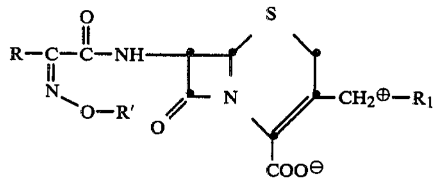

wherein R is an amino-substituted heterocyclic of the formula

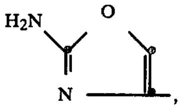, 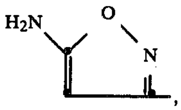, or 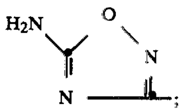;

R' is hydrogen, $C_1$–$C_4$ alkyl, a carboxy-substituted alkyl or a carboxy-substituted cycloalkyl group of the formula

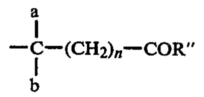

wherein a and b when taken separately are independently hydrogen or $C_1$–$C_3$ alkyl, and a and b when taken together with the carbon atom to which they are bonded form a $C_3$–$C_7$ carbocyclic ring; n is 0–3; and R'' is hydroxy, $C_1$–$C_4$ alkoxy, amino OR°, wherein R° is a carboxy-protecting group, R' is a carbamoyl group of the formula

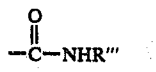

wherein R''' is $C_1$–$C_3$ alkyl, phenyl, or $C_1$–$C_3$ alkyl substituted by phenyl; $\oplus R_1$ is an oximino-substituted pyridinium, quinolinium, or isoquinolinium group represented by the formulas

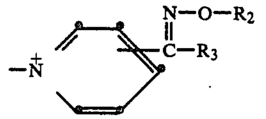

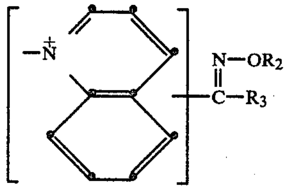

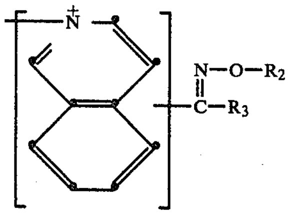

wherein $R_2$ and $R_3$ independently are hydrogen or $C_1$–$C_3$ alkyl; and the pharmaceutically acceptable non-toxic salts thereof.

2. The compound of claim 1 wherein $\oplus R_1$ is an oximino-substituted pyridinium group.

3. The compound of claim 2 wherein the pyridinium group is a 3- or 4-oximino-substituted pyridinium group of the formula

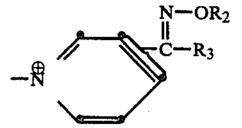

4. The compound of claim 3 wherein R is 2-aminooxazol-4-yl or 5-amino-1,2,4-oxadiazol-3-yl.

5. The compound of claim 4 wherein R' is $C_1$–$C_4$ alkyl or a group of the formula

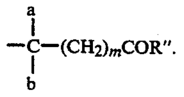

6. The compound of claim 5 wherein R'' is hydroxy or $C_1$–$C_4$ alkoxy.

7. The compound of claim 6 wherein $R_2$ is hydrogen or methyl and $R_3$ is hydrogen.

8. The compound of claim 7 wherein R is 2-aminooxazol-4-yl.

9. The compound of claim 7 wherein R is 5-amino-1,2,4-oxadiazol-3-yl.

10. The compound of claim 5 wherein R' is $C_1$–$C_4$ alkyl.

11. The compound of claim 10 wherein R is 2-aminooxazol-4-yl and R' is methyl.

12. The compound of claim 10 wherein R is 5-amino-1,2,4-thiadiazol-3-yl and R' is methyl.

13. The compound of claim 1 wherein $\oplus R_1$ is an oximino-substituted quinolinium group.

14. The compound of claim 13 wherein R is 2-aminooxazol-4-yl and R' is $C_1$–$C_4$ alkyl or a group of the formula

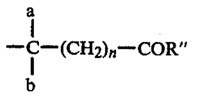

wherein R'' is hydroxy or $C_1$–$C_4$ alkoxy.

15. The compound of claim 14 wherein R' is methyl.

16. The compound of claim 13 wherein R is 5-amino-1,2,4-oxadiazol-3-yl and R' is $C_1$–$C_4$ alkyl or a group of the formula

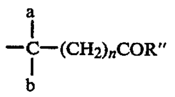

wherein R'' is hydroxy or $C_1$–$C_4$ alkoxy.

17. The compound of claim 16 wherein R' is methyl.

18. The compound of claim 1 wherein $\oplus R_1$ is an oximino-substituted isoquinolinium group.

19. The compound of claim 18 wherein R is 2-aminooxazol-4-yl and R' is $C_1$–$C_4$ alkyl or a group of the formula

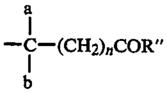

wherein R'' is hydroxy or $C_1$–$C_4$ alkoxy.

20. The compound of claim 18 wherein R is 5-amino-1,2,4-oxadiazol-3-yl and R' is $C_1$–$C_4$ alkyl or a group of the formula

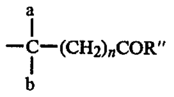

wherein R'' is hydroxy or $C_1$–$C_4$ alkoxy.

21. An antibiotic composition comprising a compound of claim 1, wherein R'' is other than a carboxy-protecting group, or a pharmaceutically acceptable non-toxic salt thereof and a pharmaceutically acceptable carrier.

22. A method for treating bacterial infections in a mammal which comprises administering in an effective dose of between about 100 mg and about 2 g of a compound of claim 1, wherein R'' is other than a carboxy-protecting group, or a pharmaceutically acceptable non-toxic salt thereof.

23. The method of claim 22 wherein $\oplus R_1$ is an oximino-substituted pyridinium group of the formula

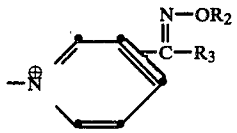
wherein $R_3$ is hydrogen or methyl and $R_2$ is hydrogen; R is 2-aminooxazol-4-yl or 5-amino-1,2,4-oxadiazol-3-yl, and R' is $C_1$–$C_4$ alkyl or a pharmaceutically acceptable non-toxic salt thereof.
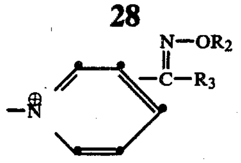
wherein $R_3$ is hydrogen or methyl and $R_2$ is hydrogen; R is 2-aminooxazol-4-yl or 5-amino-1,2,4-oxadiazol-3-yl, and R' is $C_1$–$C_4$ alkyl or a pharmaceutically acceptable non-toxic salt thereof.
* * * * *